United States Patent
Hossack et al.

[19]

[11] Patent Number: 5,971,925
[45] Date of Patent: Oct. 26, 1999

[54] BROADBAND PHASED ARRAY TRANSDUCER WITH FREQUENCY CONTROLLED TWO DIMENSIONAL APERTURE CAPABILITY FOR HARMONIC IMAGING

[75] Inventors: John A. Hossack, Palo Alto; Amin M. Hanafy, Los Altos Hill, both of Calif.

[73] Assignee: Acuson Corporation, Mountain View, Calif.

[21] Appl. No.: 09/093,422

[22] Filed: Jun. 8, 1998

[51] Int. Cl.⁶ .................................................. A61B 8/00
[52] U.S. Cl. ............................................. 600/443; 600/458
[58] Field of Search ................................... 600/459, 443, 600/447, 454, 455, 444

[56] References Cited

U.S. PATENT DOCUMENTS

| | | |
|---|---|---|
| 3,833,825 | 9/1974 | Haan . |
| 4,478,085 | 10/1984 | Sasaki . |
| 4,550,607 | 11/1985 | Masiak et al. . |
| 4,611,141 | 9/1986 | Hamada et al. . |
| 5,415,175 | 5/1995 | Hanafy et al. . |
| 5,438,998 | 8/1995 | Hanafy . |
| 5,582,177 | 12/1996 | Hanafy et al. ........................ 600/459 |
| 5,678,554 | 10/1997 | Hossack et al. . |
| 5,696,737 | 12/1997 | Hossack et al. . |
| 5,743,855 | 4/1998 | Hanafy et al. ........................ 600/459 |
| 5,792,058 | 8/1998 | Lee et al. ............................. 600/459 |

OTHER PUBLICATIONS

Schrope et al., *Stimulated Capillary Blood Flow Measurement Using a Nonlinear Contrast Agent*, (1992) pp. 134–158.

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic transducer array for harmonic imaging including an ultrasonic transducer array having a plurality of transducer elements, each of said transducer elements having a first surface and a second surface opposite of said first surface, said second surface being non-planar in an elevation direction and said second surface facing away from a region of examination when the transducer is in use. Transmit circuitry is coupled to the transducer array and is operative to cause the transducer array to emit a signal having a bandwidth controlled such that substantially no harmonic energy is transmitted. Receive circuitry is coupled to the transducer array and selectively responsive to harmonic echo information.

23 Claims, 3 Drawing Sheets

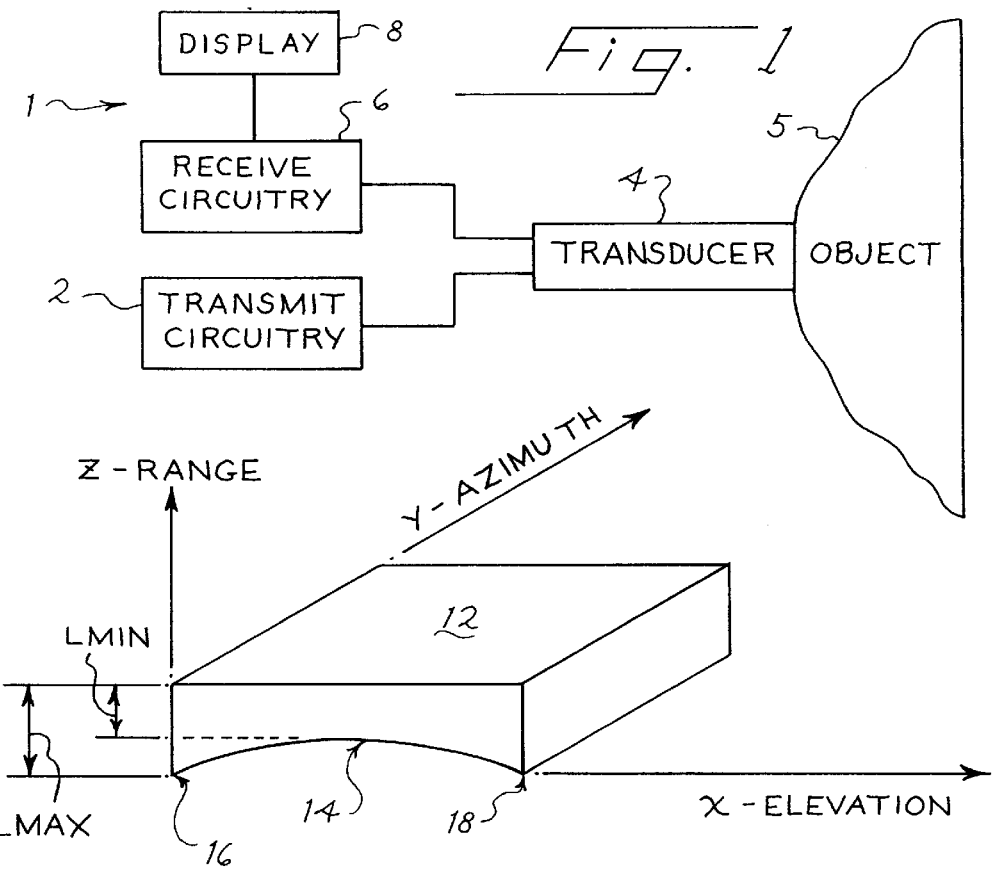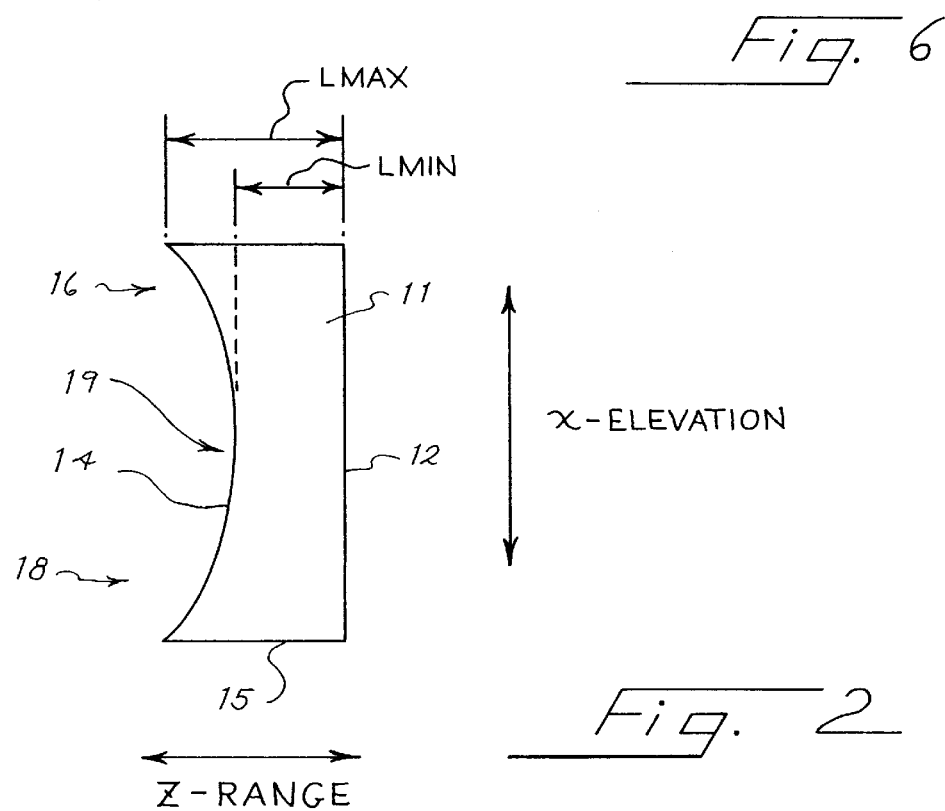

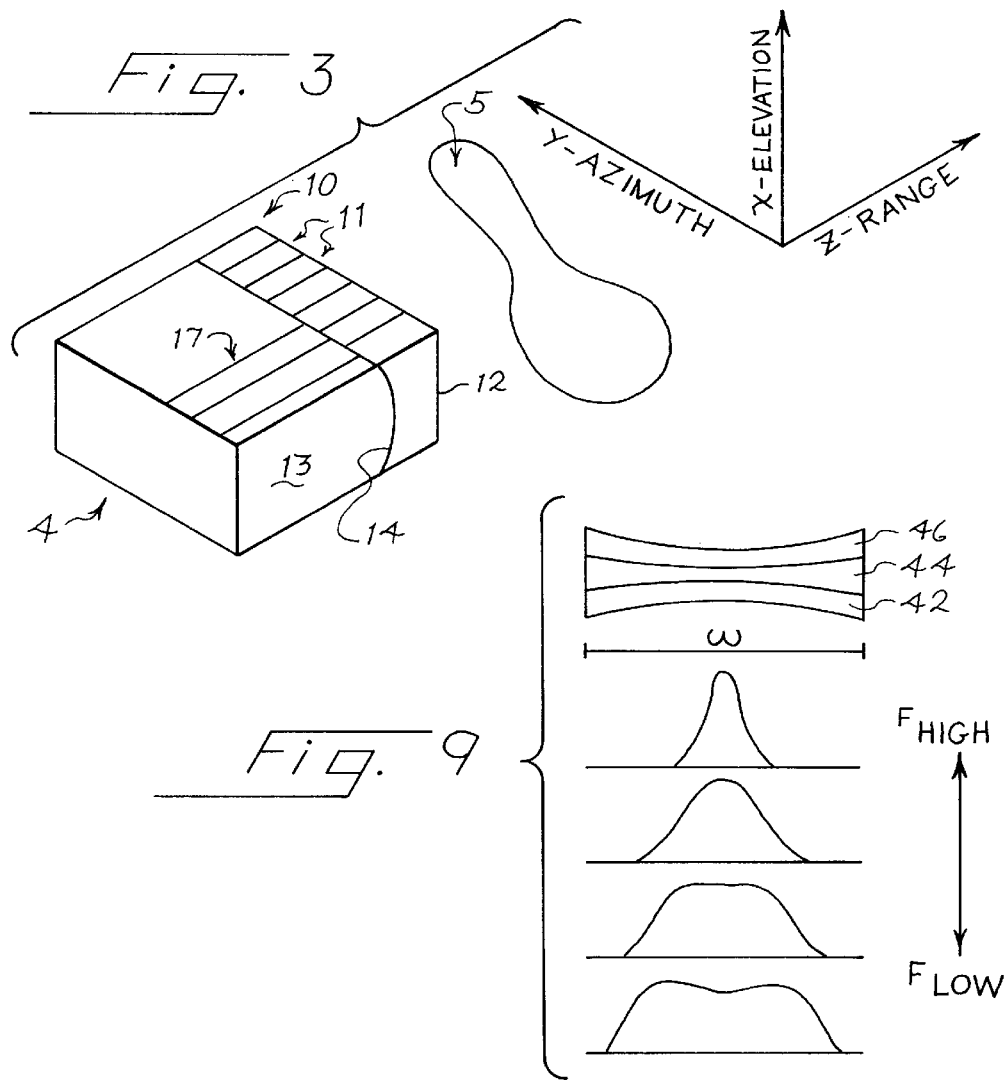
Fig. 3
Fig. 9
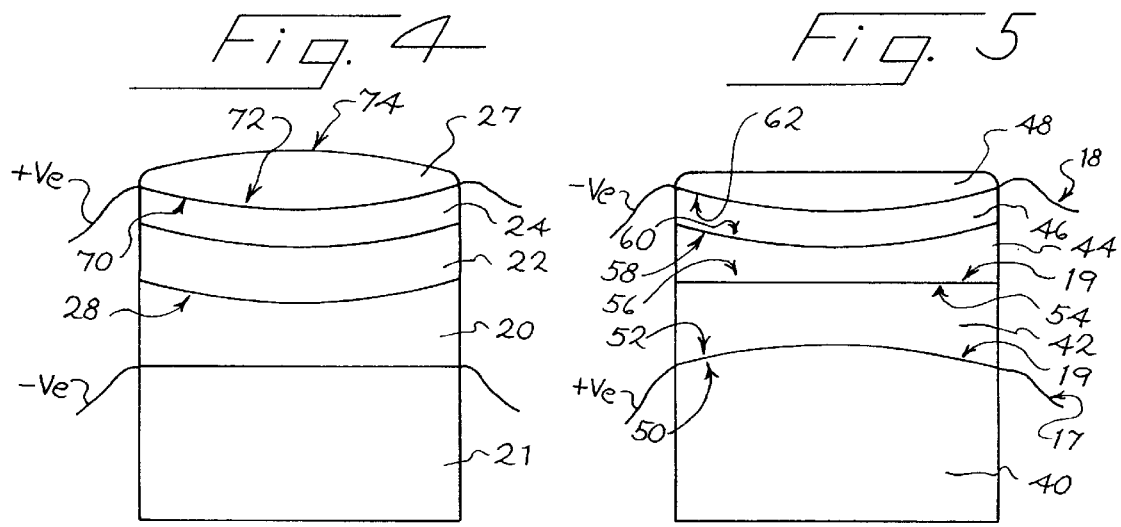
Fig. 4
Fig. 5

BROADBAND PHASED ARRAY TRANSDUCER WITH FREQUENCY CONTROLLED TWO DIMENSIONAL APERTURE CAPABILITY FOR HARMONIC IMAGING

FIELD OF THE INVENTION

This invention relates to transducers and, more particularly, a limited diffraction broadband phased array transducer with frequency controlled two dimensional aperture capability preferably for use in the medical diagnostic field.

BACKGROUND OF THE INVENTION

Ultrasound machines are often used for observing organs in the human body. Typically, these machines contain transducer arrays for converting electrical signals into pressure waves. Generally, the transducer array is in the form of a hand-held probe which may be adjusted in position to direct the ultrasound beam to a region of interest. Transducer arrays may have, for example, 128 transducer elements for generating an ultrasound beam. An electrode is formed on a top and bottom surface of each transducer element and each transducer element is individually excited to generate pressure waves as is well known. The pressure waves generated by the transducer elements are directed toward a region of examination, and more particularly, an object to be observed, such as the heart of a patient being examined. Each time the pressure wave confronts tissue having different acoustic characteristics, a wave is reflected backwards to the transducer. The array of transducer elements converts the reflected pressure waves into corresponding electrical signals. An example of a phased array acoustic imaging system is described in U.S. Pat. No. 4,550,607 which is incorporated herein by reference. That patent illustrates circuitry for combining the incoming signals received by the transducer array to produce a focused image on a display screen.

Broadband transducers are transducers capable of operating at a wide range of frequencies without a loss in sensitivity. As a result of the increased bandwidth provided by broadband transducers, the resolution along the range direction may improve, thereby resulting in better image quality. One possible application for a broadband transducer is contrast or tissue harmonic imaging. In contrast harmonic imaging, contrast agents, such as micro-balloons of protein spheres, are injected into a body to illustrate how much of a certain tissue, such as the heart, is active. These microballoons are typically one to five micrometers in diameter and, once injected into the body, may be observed via ultrasound imaging to determine the degree of blood perfusion in the tissue being examined. B. Schrope et al. "Simulated Capillary Blood Flow Measurement Using a Nonlinear Ultrasonic Contrast Agent." *Ultrasonic Imaging,* Vol. 14 at 134–58 (1992), which is incorporated herein by reference, disclose that an observer may clearly see the contrast agent at the second operating harmonic. That is, at the fundamental frequency, the heart and muscles tissue is clearly visible via ultrasound techniques. However, at the second harmonic, the observer is capable of clearly viewing the contrast agent itself. In addition, it may be desirable to provide an ultrasonic system that is responsive to reflected harmonic signals even when a contrast agent is not injected into a body because tissue itself produces a non-linear response.

Because contrast and tissue harmonic imaging requires that the transducer be capable of operating at a broad range of frequencies (i.e., at both the fundamental and second harmonic), existing transducers typically cannot function at such a broad range. For example, a transducer having a center frequency of 5 Megahertz and having a 70% ratio bandwidth to center frequency has a bandwidth of 3.25 Megahertz to 6.75 Megahertz. If the fundamental frequency is 3.5 Megahertz, then the second harmonic is 7.0 Megahertz. Thus, a transducer having a center frequency of 5 Megahertz would not be able to adequately operate at both the fundamental frequency and second harmonic frequency.

U.S. Pat. Nos. 5,415,175 ("the '175 patent") and 5,438,998 ("the '998 patent"), assigned to the present assignee and specifically incorporated herein by reference, disclose a mechanically focused transducer array in which the surface of each transducer element that faces a region of examination when the transducer is in use, is preferably concave in shape and each transducer elements has a non-uniform thickness measured in the range direction. Preferably at least one acoustic matching layer is disposed over each transducer element and the acoustic matching layer also has a non-uniform thickness and a concave surface facing the region of examination. The combination of the curved transducer element and acoustic matching layer provides focusing in the elevation direction. Typically a non-refractive protective layer such as polyurethane is placed on a front surface of the transducer array. Because each transducer element has a non-uniform thickness, by controlling the excitation frequency, an operator can control which section of the transducer element generates the ultrasound beam. At higher excitation frequencies, the beam is primarily generated from the center of the transducer element and at lower excitation frequencies, the beam is primarily generated from the full aperture of the transducer element.

U.S. Pat. No. 4,478,085 discloses an ultrasound transducer that has a plurality of transducer elements that are non-uniform in thickness. In one embodiment shown in FIGS. 8A–D of this patent, each transducer element has a front surface that faces a region of examination when the transducer is in use that is planar and a back surface, opposite of the front surface, that is concave and each transducer element has a non-uniform thickness measured in the range direction. A single matching layer 32 is disposed over the transducer element 31 and an acoustic lens 33 is disposed on the matching layer. Sasaki does not provide details regarding the acoustic lens material, however, the lens has a convex/concave shape and is probably lossy. In addition to having a transducer which is capable of operating at a broad range of frequencies, two-dimensional transducer arrays are also desirable to increase the resolution of the images produced. An example or a two-dimensional transducer array is illustrated in U.S. Pat. No. 3,833,825 to Haan issued Sep. 3, 1974 and is incorporate herein by reference. Two-dimensional arrays allow for increased control of the excitation of ultrasound beams along the elevation axis, which is otherwise absent from conventional single-dimensional arrays. However, two-dimensional arrays are also difficult to fabricate because they typically require that each element be cut into several segments along the elevation axis, connecting leads for exciting each of the respective segments. A two-dimensional array having 128 elements in the azimuthal axis, for example, would require at least 256 segments, two segments in the elevation direction, as well as interconnecting leads for the segments. In addition, they require rather complicated software in order to excite each of the several segments at appropriate times during the ultrasound scan because there would be at least double the amount of segments which would have to be individually excited as compared with a one-dimensional array.

It is thus desirable to provide a transducer array that employs a low loss acoustic lens and a plurality of sharply focused acoustic matching layers. It is also desirable to provide a transducer array that provide 1.5 or 2 dimensional imaging without the system complexity or channels required of typical 1.5 and 2 dimensional arrays.

BRIEF DESCRIPTION OF THE DRAWINGS

FIG. 1 is a schematic view of an ultrasound system for generating an image of an object or body being observed in a region of examination.

FIG. 2 is a cross-sectional view taken along the elevation direction of a transducer element according to a preferred embodiment of the present invention.

FIG. 3 is a perspective view of a broadband transducer array further illustrating the transducer shown in FIG. 1 according to a preferred embodiment of the present invention.

FIG. 4 is a cross-sectional view taken along the elevation direction of a transducer element according to the prior art.

FIG. 5 is a cross-sectional view taken along the elevation direction of a transducer element according to a preferred embodiment of the present invention.

FIG. 6 is an enlarged view of a single broadband transducer element of the transducer array constructed in accordance with the present invention.

FIG. 9 is a view of the exiting beam profile produced by the broadband transducer elements from low to high frequencies as compared to the width of the transducer element according to a preferred embodiment of the present invention.

SUMMARY OF THE INVENTION

Figure 7:
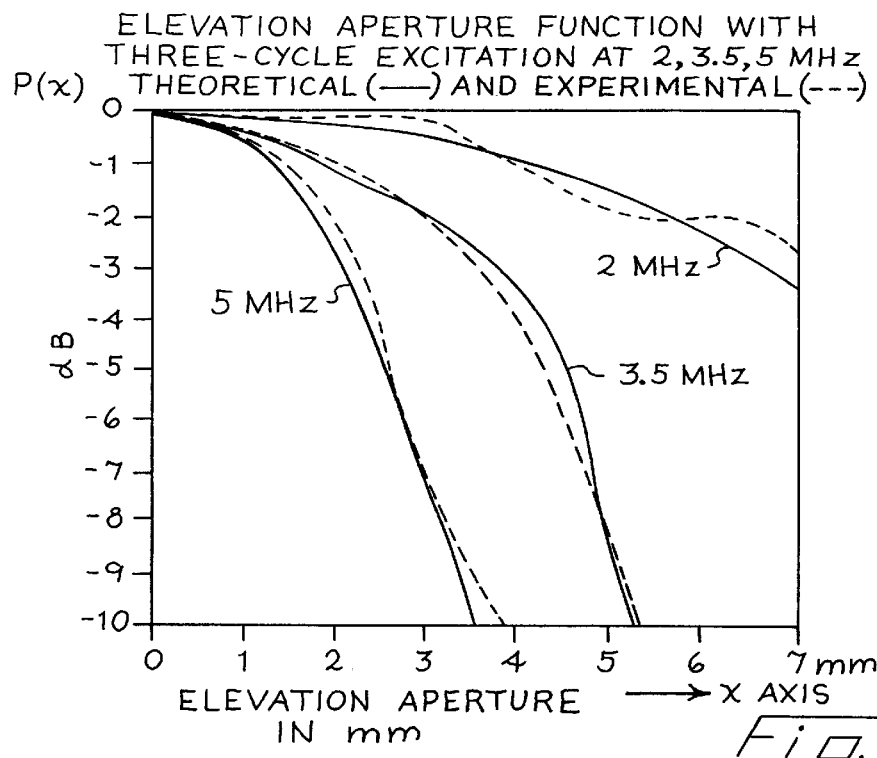
FIG. 7 is a graph of the elevation aperture function output by a transducer according to a preferred embodiment of the present invention.
Figure 8:
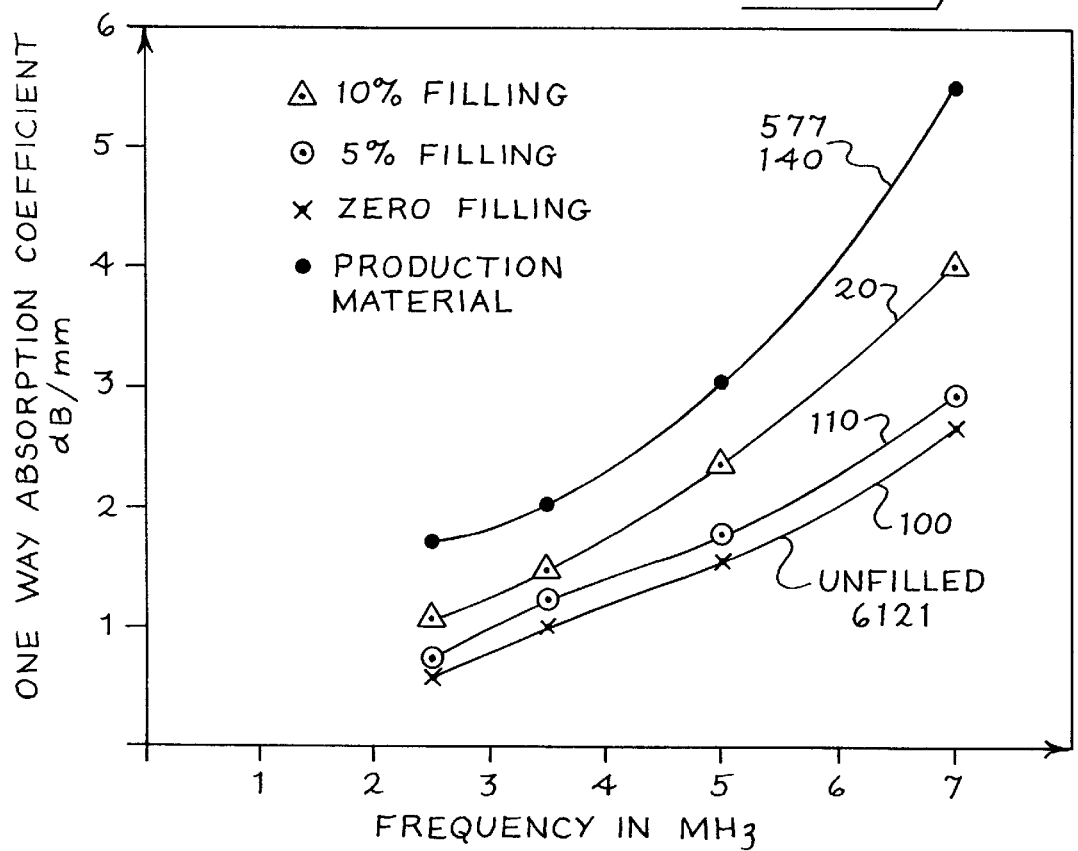
FIG. 8 is a graph comparing one way absorption coefficient versus frequency of RTV 577, X3-6121, and modified X3-6121.

According to a first aspect of the invention thee is provided a method for ultrasonically imaging a target during an imaging session, said method comprising the following steps:

(a) transmitting ultrasonic energy at a fundamental frequency into the target from a plurality of transducer elements, each of said transducer elements having a first surface and a second surface opposite of said first surface, said second surface being non-planar in an elevation direction and said second surface facing away from a region of examination when the transducer is in use; and (b) receiving ultrasonic echo information at a second harmonic from the target while filtering out ultrasonic echo information at the fundamental frequency.

According to a second aspect of the invention there is provided an ultrasonic imaging system comprising:

an ultrasonic transducer array comprising a plurality of transducer elements, each of said transducer elements having a first surface and a second surface opposite of said first surface, said second surface being non-planar in an elevation direction and said second surface facing away from a region of examination when the transducer is in use; and transmit circuitry coupled to the transducer array, said transmit circuitry operative to cause the transducer array to emit a signal having a bandwidth controlled such that substantially no harmonic energy is transmitted; and receive circuitry coupled to the transducer array and selectively responsive to harmonic echo information.

DETAILED DESCRIPTION OF THE PRESENTLY PREFERRED EMBODIMENTS

FIG. 1 is a schematic view of an ultrasound system for generating an image of an object or body 5 being observed in a region of examination. The ultrasound system 1 has transmit circuitry 2 for transmitting electrical signals to the transducer 4, receive circuitry 6 for processing the signals received by the transducer 4 and a display 8 for displaying the image of the object 5 being observed. The transducer 4 may be a hand-held model and can be adjusted in position to direct the ultrasound beam to a region of examination 5.

Referring to FIG. 3, the transducer 4 includes an array 10 formed of a plurality of transducer elements 11. Typically there are one hundred and twenty eight elements sequentially arranged along the azimuth axis, however, the array 10 may include any number of transducer elements. The transducer array 10 is supported on a backing block 13. Signal leads 17 couple the electrode of each transducer element 11 to the transmit and receive circuitry as is well known. The transducer elements 11 convert electrical signals provided by the transmit circuitry to pressure waves. The transducer elements 11 also convert pressure waves reflected from the object 5 in the region of examination into electrical signals which are then processed in the receive circuitry 6 and ultimately displayed on display 8. For purposes of clarity, not all of the elements of the transducer 4 have been illustrated.

Referring to FIGS. 2 and 3, each of the plurality of transducer elements 11 according to a preferred embodiment of the present invention has a front surface 12, a back surface 14, a center portion 19, and two side portions 16, 18. The front surface 12 is the surface which faces the region of examination when the transducer is in use. The back surface 14 is preferably curved in the elevation direction and, more preferably, is concave in shape. The front surface 12 is preferably generally or substantially planar. In one preferred embodiment the thickness of each transducer element, measured in the range direction, is at a maximum LMAX at each of the side portions 16 and 18 and a minimum LMIN at substantially the center portion 19. However, each of the sides 16, 18 do not have to be the same thickness and LMIN does not have to be located in the exact center of each transducer element. For example, each transducer element may be thinnest at one end and gradually increase in thickness along the elevation direction so that it is thickest at an opposite end such as that described in U.S. Pat. No. 5,678,554. The term side portion 16, 18 refers not only to the sides 15 of the respective elements 11, but may also include a region interior to the element 11 where the thickness of the element is greater than the thickness in the center portion 19. The radius of curvature along the elevation direction may be different from the radius of curvature along the azimuth direction for curvilinear array application. In a linear or sector application, the radius of curvature along the azimuth direction is infinite.

FIG. 4 is a cross-sectional view taken in the elevation direction of a transducer element as described in the '175 and '998 patents previously mentioned. As previously described, each transducer element includes a layer 20 of transducer material that is disposed on a backing block 21, as well as a first acoustic matching layer 22, a second acoustic matching layer 24, and a coupling element 27 preferably formed of unfilled polyurethane. The transducer layer is of non-uniform thickness and has a curved front surface 28. Because the shape of the layer of transducer material 20 with its curved surface facing a region of examination when the transducer is in use provides focusing in the elevation direction, the coupling element 27 need not be refracting. Matching layer 22 is preferably a high impedance matching layer and matching layer 24 is a low impedance matching layer.

FIG. 5 is a cross-sectional view taken along the elevation direction of a transducer element according to a preferred embodiment of the present invention. The transducer includes a backing block 40, a layer of transducer material 42, preferably a material exhibiting piezoelectric characteristics, a first acoustic matching layer 44, a second acoustic matching layer 46 and a focusing lens 48 stacked in the order shown in FIG. 5. Alternatively only one acoustic matching layer may be used or more than two acoustic matching layers may be used. The layer of transducer material 42 is of non-uniform thickness measured along the range axis. The layer of transducer material 42 has a back surface 52 which faces away from a region of examination when the transducer is in use that is non-planar and, more preferably, concave in shape. The backing block 40 preferably has a curved top surface 50 to accommodate the back surface 52 of the layer of transducer material 42. The front surface 54 of the layer of transducer material is preferably substantially planar. Electrodes 19 are formed on the front and back surfaces 54, 52 of the layer of transducer material 42. The first acoustic matching layer 44 is of non-uniform thickness and has a planar back surface 56 and a curved front surface 58. The second acoustic matching layer 46 has a curved back surface 60 disposed of the front surface 58 of the first acoustic matching layer and a curved front surface 62.

FIG. 6 is an enlarged view of a single broadband transducer element of the transducer element according to a preferred embodiment of the present invention. In a preferred embodiment, the front surface 12 which will face a region of examination when the transducer is in use is substantially planar and the back surface 14 which will face away from a region of examination when the transducer is in use is concave.

Unlike the transducer disclosed in the '175 and '998 patents and shown in FIG. 4, the front surface 54 of each transducer element 42 is substantially planar and thus does not, by itself, provide focusing in the elevation direction. Instead an ultrasound beam emitted by the layer of transducer material having a shape according to the present invention is defocused or divergent in the elevation direction. In order to focus the emitted beam, matching layers having a concave surface facing the region of examination and a focusing lens 48 disposed over the acoustic matching layers 44, 46, i.e., on the front surface of the transducer array are used. The concave surface of the matching layers cause a converging lens effect. By combining transducer elements having the shape according to the present invention with the matching layers and a planoconvex focusing lens, elevational focusing such as that described in the '175 and '998 patents can be achieved.

In a preferred embodiment the various elements of the transducer according to the present invention are formed of the following materials. The layer of transducer material 42 is a piezoelectric ceramic such as HD3203 available from Motorola of Albuquerque, N. Mex. or a composite. The first acoustic matching layer 44 is made from DER 332 and DEH 24 available from Dow Corning plus 9 micron Alumina particles forming a material with a longitudinal velocity of 2064 m/s and a density of 4450 kg/m$^3$. The second acoustic matching layer 46 is made from DER 332 and DEH 24 available from Dow Corning having a longitudinal velocity of 2630 m/s and a density of 1200 kg/m3. The backing block 40 is a filled epoxy comprising Dow Corning's part number DER 332 treated with Dow Corning's curing agent DEH 24 and an aluminum oxide filler. Lens 48 is made from a room-temperature-vulcanized silicone such as RTV 577 silicone available from Dow Corning or a room-temperature-vulcanized silicone elastomer such as RTV X3-6121 also available dfrom Dow Corning preferably modified by adding aluminum oxide ($Al_2O_3$) having 1 $\mu$m particle size in order to match the lens 48 to the acoustics in the body. In a preferred embodiment 5% by weight of aluminum oxide is added although the percent added may range from 0% to 10%.

It is desirable for the lens to have a minimum insertion loss preferably $\leq$2.0 dB/mm, one way at 5 Mega Hertz at a velocity of sound of about 1000 meters/sec, Modified RTV X3-6121 satisfies these conditions.

Table 1 below compares the attenuation of RTV 577, modified X3-6121 and unmodified X3-6121.

TABLE 1

| Frequency (MHz) | Attenuation: One Way (dB/mm) | | |
|---|---|---|---|
| | RTV 577 | Modified X3-6121 | Unmodified X3-6121 |
| 2.5 | 1.68 | 0.75 | 0.6 |
| 3.5 | 2 | 1.22 | 1.00 |
| 5 | 3 | 1.78 | 1.50 |
| 7 | 5.5 | 2.93 | 2.60 |

Table 2 compares other properties of RTV577, modified X3-6121 and unmodified X3-6121.

TABLE 2

| | RTV 577 | Modified X3-6121 | Unmodified X3-6121 |
|---|---|---|---|
| Acoustic Impedance ($10^5$ gm/cm$^{-2}$ sec) | 1.32 | 1.31 | 1.26 |
| Sound Velocity ($\times 10^3$ meter/sec) | 1.035 | 1.102 | 1.00 |
| Reflection Coefficient (relative to Z = 1.54) | 8% | 8% | |
| Thermal Conductivity (w/m C°) | 0.24 | 0.227 | |
| Tear Resistance (PPI) | 90 | 80 | |
| Dielectric Strength (volt/mil) | 450 | 500 | |

A transducer formed according to the present invention has enhanced performance to insure that the insertion loss of the lens material will not distort the exiting pressure function of the transducer. Hence, the lower sidelobe single beam radiation pattern shown in FIG. 9 is maintained.

The design of the transducers disclosed in the '175 and '998 patents was used to determine the design parameters needed for the transducer according to the present invention as shown in FIG. 5. It was assumed that the same materials as described above are used. The following design parameters of the transducer design disclosed in the '175 and '998 patent as shown in FIG. 4 of this application were used:

layer of piezoelectric material 20
  Width in the elevation direction W=14 millimeters
  Width from the center of each element to a side WC=7 millimeters
  LMIN=0.368 millimeters
  LMAX=0.673 millimeters
acoustic matching layer 22
  LMIN=0.165 millimeters
  LMAX=0.305 millimeters
acoustic matching layer 24
  LMIN=0.188 millimeters
  LMAX=0.330 millimeters The layers are stacked in the order shown in FIG. 4 and the composite height difference, $\Delta_{Height}$, between the end of a transducer element and its center is 0.587 millimeters.

Using a small arc approximation, the radius of curvature of the front surface 70 of acoustic matching layer 24 is determined by equation (1):

$$R = W_c^2/2\Delta_{Height} = 41.7 \text{ millimeters}, \tag{1}$$

where WC=7 millimeters and $\Delta_{Height}$=0.587.

In designing the transducer elements according to the present invention, it is desired to replicate the focusing effect of three elements of the prior art transducer shown in FIG. 4, namely the curvature of the front acoustic matching layer surface 70, the curvature 72 of the non-refracting layer 26 adjacent to front matching layer, and the curvature of the lens' front surface 74. The compound focus effect of these three factors must equal a focus of 41.7 millimeters as determined by equation (2):

$$1/F_{(matching\ layer\ surface\ 70)} + 1/F_{(lens\ rear\ surface\ 72)} + 1/F_{(lens\ front\ surface\ 74)} = 1/41.7, \tag{2}$$

where F=focal length.

Now assuming the front lens surface 74 is imposed as a design choice, for example, a radius of 127 millimeters is chosen for patient comfort, using the lens equation (3) this equates to a focus at 227 millimeters.

$$F(\text{lens}) = \frac{R(\text{surface 74})}{\left[\frac{V(\text{water})}{V(\text{lens})} - 1\right]} \tag{3}$$

which equals 227 when $V_{(water)}$=1520 m/s, $V_{(lens)}$=975 m/s, $R_{(surface\ 74)}$=127 millimeters.

The focal length of the lens rear surface 72 can be related to the radius of the front acoustic matching layer 70 since they are adhered to one another. Using the lens equation (3) above:

$$F(\text{lens rear surface 72}) = \frac{R(\text{matching layer surface 70})}{\left[\frac{V(\text{water})}{V(\text{lens})} - 1\right]}$$

Substituting this into equation (2), the radius of the matching layer surface 62 for the transducer according to a preferred embodiment of the present invention as shown in FIG. 5 is determined as:

$$(1.0 + 0.559)/\text{radius}_{(matching\ layer\ 62)} + 1/F_{(lens\ front\ surface)} = 1/41.7,$$

thus the radius of matching layer surface 62=79.7 millimeters. The height difference between the center and edge of the front matching layer 46 is thus $7^2/(2 \times 79.7)$=0.307 millimeters.

Thus by using an acoustic matching layer having a front surface 62 with a radius of curvature of 79.7 millimeters instead of 41.7 millimeters as for the design shown in FIG. 4, the layer of piezoelectric material 42 can be positioned in an inverted position as shown in FIG. 5 and yet the same elevation focusing as that shown in the prior art can be achieved.

While in a preferred embodiment the plurality of elements 11 are formed of a piezoelectric material, they may alternatively be formed of a composite material such as that disclosed in the '175 and '998 patents, or polyvinylidene fluoride or other suitable materials exhibiting piezoelectric characteristics.

As previously mentioned, electrodes 19 are appropriately placed on the front and back surfaces of each element 11 in order to excite the element 11 to produce an ultrasound beam, as is well known to those of ordinary skill in the art. An example of the placement of electrodes in relation to the piezoelectric material is illustrated in U.S. Pat. No. 4,611,141 which is hereby specifically incorporated herein by reference. As is commonly known in the industry, electrodes may be disposed on the piezoelectric layer by use of sputtering techniques. An interconnect flex circuit 17 is disposed between the top surface 50 of the backing block 40 and the electrode 19 on the back surface 52 of the layer of transducer material 11. Flex circuit 17 preferably applies an excitation signal to each transducer element and is commonly known as the "hot" lead. A second flex circuit 18 is disposed over the top surface of the second acoustic matching layer 46 and is preferably referenced to ground. Alternatively, the ground electrode may be a simple non-patterned foil, such as a golded plated mylar film, for example. The acoustic matching layers are metalized on their sides so that the electrode 19 formed on the top surface of the transducer layer 42 is in electrical contact with the electrode formed on the top surface 62 of the second acoustic matching layer 46 and thus the second flex circuit 18. An interconnect flex circuit such as that available from Sheldahl of Northfield, Minn., may be bonded to the transducer electrodes with a fine epoxy layer.

FIG. 9 illustrates the typical variation in the beam aperture function along the elevation direction produced by the broadband transducer from low to high frequencies in accordance with a preferred embodiment of the present invention. At high frequencies such as 7 Mega hertz the beam has a narrow aperture. When the frequency is lowered, the beam has a wider aperture. Further, at low enough frequencies, such as 2 Mega hertz, the beam is effectively generated from the full aperture of the transducer. As shown in FIG. 9, the exiting pressure wave has two peaks, simulating the excitation of a wide aperture two-dimensional transducer array at lower frequencies.

In addition, when performing contrast harmonic imaging, in the transmit mode, the transducer array elements 11 may first be excited at a dominant fundamental frequency such as 3.5 Megahertz to observe the heart or other tissues and then, in receive mode, the receive circuitry filters out all frequencies but a harmonic frequency, preferably the second harmonic, in order to make the contrast agent more clearly visible relative to the tissue. This enables the observer to ascertain the degree of blood perfusion in the tissue. When observing the fundamental frequency, filters, i.e., electrical filters, centered around the fundamental frequency may be used. For example U.S. Pat. No. 5,696,737 which is hereby incorporated herein by reference and assigned to the present assignee discloses an ultrasonic imaging system and method that includes a transmit waveform generator coupled to a transducer array that causes the transducer array to emit a signal having a bandwidth controlled such that substantially no second harmonic energy is transmitted and it discloses a receiver coupled to the transducer array which is selectively responsive to second harmonic echo information. The transmit generator may include a low-pass filter to control the bandwidth of the emitted signal. The receiver may include a time-varying frequency filter responsive to second harmonic echo information. For further details reference is made to U.S. Pat. No. 5,696,737. When observing the second harmonic, filters centered around the second harmonic frequency may be used. Although the transducer may be set in the receive mode at the second harmonic as described above, the transducer array may be capable of transmitting and receiving at the fundamental frequency and its second harmonic frequency. As used herein, "harmonic" is intended broadly to include subharmonics and fractional harmonic energy (e.g. ½ or ³⁄₂ of the fundamental), as well as higher harmonics (e.g. 2 or 3 times the fundamental). The ultrasound transducer according to the present invention may be used selectively for fundamental imaging, harmonic imaging or a combination of fundamental and harmonic imaging. For example, U.S. Ser. Nos. 08/904,829 and 08/838,920, which is assigned to the present assignee and hereby incorporated by reference, discloses such methods.

The transducer designed according to the present invention provides limited diffraction in both the near and far fields with a single beam throughout the entire field and without sidelobes in the far field. Also, the typical maxima and minima in the near field of conventional transducers are eliminated thereby resulting in clear images free from sidelobe scatter artifact.

In addition, due to the non-uniform thickness of the piezoelectric layer in the elevation direction, the radiating aperture or slice thickness of the transducer array is frequency dependent which allows the transducer to perform as a 1.5 or 2 dimensional transducer without requiring system hardware complexity or the additional cabling of traditional 1.5 and 2 dimensional transducers. Instead, aperture control is achieved through software control of the transmitter spectral output or the receiver filter characteristics.

Finally the transducer array according to the present invention provides increased bandwidth due to the non-uniform thickness of the layer of transducer material.

FIG. 7 is a graph of the elevation aperture function for a transducer designed according to the present invention. The elevation axis is plotted along the horizontal axis in millimeters and the aperture function P(x) is plotted along the vertical axis in decibels. The elevation aperture function is plotted for three frequencies, namely, 2 MHz, 3.5 MHz and 5 MHz. Theoretical data is plotted in solid line and experimental data is plotted in dotted line. The experimental data was carried out using a transducer as shown in FIG. 5 with a lens 48 formed of modified X3-6121. It can be seen from the graphs that at 3.5 and 5 MHz no sidelobes were generated but at 2 MHz sidelobes were generated. Using standard silicone for the lens would have resulted in increased sidelobe level at all frequencies. The limited diffraction offered by the variable thickness crystal is dependent of the aperture function P(x) shown in FIG. 7, since at 3.5 and 5 MHz, the aperture function satisfies the condition given by equation (4) both in the near and far field i.e., $$Z \gg \frac{k(x^2 + y^2)_{max}}{2}, \quad (4)$$

where Z is range and k is $2\pi/\lambda$.

The radiation pattern in the whole field is given by equation (5) as the Fourier transform of P(x) giving a single beam without sidelobes.

$$P(x_0) = \int_{-T}^{T} P_x(x) \exp\left[-J\frac{2\pi}{\lambda z}(x_0 x)\right] dx. \quad (5)$$

Eq. 5 shows that the radiation pattern in the entire field is given by the Fourier transform of the radiating aperture.

It can be seen from these graphs that as the excitation frequency increases the width of the emitted ultrasound beam decreases.

It is to be understood that the forms of the invention described herewith are to be taken as preferred examples and that various changes in the shape, size and arrangement of parts may be resorted to without departing from the spirit of the invention or the scope of the claims.

What is claimed is:

1. A method for ultrasonically imaging a target during an imaging session, said method comprising the following steps:

(a) transmitting ultrasonic energy at a fundamental frequency into the target from a plurality of transducer elements, each of said transducer elements having a first surface and a second surface opposite of said first surface, said second surface being non-planar in an elevation direction and said second surface facing away from a region of examination when the transducer is in use; and (b) receiving ultrasonic echo information at a harmonic from the target while filtering out ultrasonic echo information at the fundamental frequency.

2. The method according to claim 1 wherein the transmitting step (a) comprises the step of controlling bandwidth of the transmitted ultrasonic energy to substantially prevent transmission of ultrasonic energy at a harmonic of the fundamental frequency.

3. The method according to claim 1 wherein the transmitting step (a) comprises the step of controlling bandwidth of the transmitted ultrasonic energy to substantially prevent transmission of ultrasonic energy at a second harmonic of the fundamental frequency.

4. The method according to claim 1 wherein the receiving step (b) comprises the step of using a time-varying frequency filter to filter out ultrasonic echo information at the fundamental frequency.

5. The method according to claim 1 further providing the steps of (c) processing the received ultrasonic echo information at the second harmonic; and (d) displaying the echo information.

6. The method of claim 1 wherein said target is free of contrast agent throughout the entire imaging session.

7. The method of claim 1 further comprising the step of injecting a contrast agent into the target before or during the imaging session.

8. The transducer array of claim 1 wherein each of said transducer elements has a thickness measured in a range direction between the first and second surface wherein each transducer element has a minimum thickness located at about a center of each of the plurality of transducer elements and each transducer element has a maximum thickness located at each end of each transducer element.

9. An ultrasonic imaging system comprising:

an ultrasonic transducer array comprising a plurality of transducer elements, each of said transducer elements having a first surface and a second surface opposite of said first surface, said second surface being non-planar in an elevation direction and said second surface facing away from a region of examination when the transducer is in use; and transmit circuitry coupled to the transducer array, said transmit circuitry operative to cause the transducer array to emit a signal having a bandwidth controlled such that substantially no harmonic energy is transmitted; and receive circuitry coupled to the transducer array and selectively responsive to harmonic echo information.

10. The ultrasonic imaging system of claim 9 wherein the receive circuitry comprises a time-varying frequency filter responsive to second harmonic echo information.

11. The system of claim 9 wherein the second surface is a curved surface in the elevation direction.

12. The system of claim 11 wherein a first surface is a planar surface in the elevation direction.

13. The system of claim 9 wherein the second surface is concave and the first surface is planar in the elevation direction.

14. The system of claim 9 further comprising a focusing lens disposed on the first surface of each transducer element.

15. The system of claim 14 wherein the focusing lens is made of a silicone elastomer modified with a percentage of aluminum oxide.

16. The system of claim 15 wherein the percentage ranges from 0% to 10% by weight.

17. The system of claim 15 wherein the percentage is 5% by weight.

18. The system of claim 9 further comprising a backing block having a top surface on which is disposed the second surface of the plurality of transducer elements, wherein the top surface of the backing block is complementary in shape to the second surface of each of the plurality of transducer elements.

19. The system of claim 9 further comprising at least one acoustic matching layer disposed on the first surface of each of the plurality of transducer elements.

20. The system of claim 19 wherein the at least one acoustic matching layer has a non-uniform thickness measured in a range direction.

21. The system according to claim 7 wherein the transducer elements are formed of piezoelectric material or composites.

22. The system according to claim 13 wherein the focusing lens is a converging lens.

23. The transducer array of claim 9 wherein each of said transducer elements has a thickness measured in a range direction between the first and second surface wherein each transducer element has a minimum thickness located at about a center of each of the plurality of transducer elements and each transducer element has a maximum thickness located at each end of each transducer element.

* * * * *

UNITED STATES PATENT AND TRADEMARK OFFICE
CERTIFICATE OF CORRECTION

PATENT NO. : 5,971,925

DATED : October 26, 1999

INVENTOR(S) : John A. Hossack et al.

It is certified that error appears in the above-identified patent and that said Letters Patent is hereby corrected as shown below:

In column 2, line 49, please change "or" to --of--.

In column 3, line 41, please change "thee" to --there--.

In column 6, line 21, please insert --$\alpha$-- before "$\leq$".

In column 7, line 1, please insert --:-- (colon) after "20".

In column 7, line 3, please change "WC=7" to --$W_C=7$--.

In column 7, line 7, please insert --:-- (colon) after "22".

In column 7, line 10, please insert --:-- (colon) after "24".

In column 7, line 21, please change "WC=7" to --$W_C=7$--.

Signed and Sealed this

Tenth Day of April, 2001

Attest:

NICHOLAS P. GODICI

Attesting Officer

Acting Director of the United States Patent and Trademark Office